United States Patent [19]

Ward et al.

[11] 4,209,010

[45] Jun. 24, 1980

[54] ARTIFICIAL SPHINCTER

[75] Inventors: Bruce D. Ward, Barrington; Alfred R. Perlin, Highland Park, both of Ill.

[73] Assignee: The Kendall Company, Boston, Mass.

[21] Appl. No.: 928,140

[22] Filed: Jul. 26, 1978

[51] Int. Cl.$^2$ .............................................. A61B 19/00
[52] U.S. Cl. .................... 128/1 R; 128/283; 128/DIG. 25
[58] Field of Search ............... 128/283, DIG. 25, 1 R, 128/335, 371, 270; 3/1, 1.1; 428/900

[56] References Cited

U.S. PATENT DOCUMENTS

| | | | |
|---|---|---|---|
| 1,810,466 | 6/1931 | Deutsch | 128/348 |
| 2,243,529 | 5/1941 | Grossman et al. | 128/283 |
| 2,324,520 | 7/1943 | Lamson | 128/283 |
| 2,455,859 | 12/1948 | Foley | 128/346 |
| 2,494,393 | 1/1950 | Lamson | 128/1 |
| 2,510,766 | 6/1950 | Surface | 128/1 |
| 2,533,924 | 12/1950 | Foley | 128/346 |
| 2,543,773 | 3/1951 | Goldschmidt | 32/2 |
| 2,564,399 | 8/1951 | Franken | 128/283 |
| 2,638,093 | 5/1953 | Kulick | 128/133 |
| 2,649,086 | 8/1953 | Slutjer | 128/1 R |
| 2,649,854 | 8/1953 | Salm | 128/1 |
| 2,655,195 | 10/1953 | Curtis | 428/195 |
| 2,703,576 | 3/1955 | Furr, Jr. | 128/283 |
| 3,066,667 | 12/1962 | Berry | 128/1 |
| 3,080,865 | 3/1963 | Vincent | 128/98 |
| 3,083,704 | 4/1963 | Swearingen | 128/1 |
| 3,147,754 | 9/1964 | Koessler | 128/346 |
| 3,155,096 | 11/1964 | Outwin | 128/346 |
| 3,203,421 | 8/1965 | Bialick | 128/346 |
| 3,216,420 | 11/1965 | Smith et al. | 128/283 |
| 3,253,594 | 5/1966 | Matthews et al. | 128/343 |
| 3,372,695 | 3/1968 | Beliveau et al. | 128/1 |
| 3,384,073 | 5/1968 | Van Winkle, Jr. | 128/1 |
| 3,419,008 | 12/1968 | Plishner | 128/346 |
| 3,447,533 | 6/1969 | Spicer | 128/283 |
| 3,503,400 | 3/1970 | Osthagen et al. | 128/349 |
| 3,538,917 | 11/1970 | Selker | 128/326 |
| 3,554,184 | 1/1971 | Habib | 128/1 |
| 3,565,073 | 2/1971 | Glesy | 128/283 |
| 3,575,158 | 4/1971 | Summers | 128/1 |
| 3,613,661 | 10/1971 | Shah | 128/1 R |
| 3,616,145 | 10/1971 | Clifton | 428/900 |
| 3,642,004 | 2/1972 | Osthagen et al. | 128/349 R |
| 3,646,616 | 3/1972 | Keshin | 3/1 |
| 3,646,929 | 3/1972 | Bonnar | 128/1 R |
| 3,650,275 | 3/1972 | Von Der Mozel | 128/407 |
| 3,705,575 | 12/1972 | Edwards | 128/1 R |
| 3,705,580 | 12/1972 | Gauthier | 128/79 |
| 3,730,186 | 5/1973 | Edmunds, Jr. et al. | 128/325 |
| 3,731,670 | 5/1973 | Loe | 128/1 R |
| 3,744,063 | 7/1973 | McWhorter et al. | 3/1 |
| 3,750,194 | 8/1973 | Summers | 3/1 |
| 3,758,073 | 9/1973 | Schutte | 251/342 |
| 3,768,102 | 10/1973 | Kwan-Gett | 3/1 |
| 3,789,828 | 2/1974 | Schutte | 128/1 R |
| 3,797,478 | 3/1974 | Adrian et al. | 128/1 R |
| 3,810,259 | 5/1974 | Summers | 3/1 |
| 3,812,841 | 5/1974 | Issacson | 128/1 R |
| 3,815,576 | 6/1974 | Balabian | 128/1 R |
| 3,815,577 | 6/1974 | Bucalo | 128/1 R |
| 3,817,237 | 6/1974 | Bolduc | 128/1 R |
| 3,841,304 | 10/1974 | Jones | 128/1 R |
| 3,854,469 | 12/1974 | Giori | 128/1 R |
| 3,863,622 | 2/1975 | Buuck | 128/1 R |
| 3,866,611 | 2/1975 | Baumrucker | 128/346 |
| 3,875,928 | 4/1975 | Angerchik | 128/1 R |
| 3,903,894 | 9/1975 | Rosen et al. | 128/346 |
| 3,924,631 | 12/1975 | Mancusi | 128/346 |
| 3,926,175 | 12/1975 | Allen et al. | 128/1 R |
| 3,939,821 | 2/1976 | Roth | 128/1 R |
| 3,952,726 | 4/1976 | Hennig et al. | 128/1 R |
| 4,019,498 | 4/1977 | Hawtrey et al. | 128/1 R |
| 4,019,499 | 4/1977 | Fitzgerald | 128/1 R |
| 4,024,855 | 5/1977 | Bucalo | 128/1 R |
| 4,030,500 | 6/1977 | Ronquist | 128/283 |
| 4,050,461 | 9/1977 | Ruby | 128/227 |
| 4,054,140 | 10/1977 | Etes | 128/283 |
| 4,154,226 | 5/1979 | Hennig | 128/1 R |

FOREIGN PATENT DOCUMENTS

| | | | |
|---|---|---|---|
| 2717607 | 10/1978 | Fed. Rep. of Germany | 128/DIG. 25 |
| 842480 | 7/1960 | United Kingdom | 40/621 |
| 950277 | 2/1964 | United Kingdom | 428/900 |

*Primary Examiner*—John D. Yasko
*Attorney, Agent, or Firm*—Powell L. Sprunger

[57] ABSTRACT

An artificial sphincter for closure of a channel in a patient's body communicating with an opening adjacent the outside of the patient's body. The sphincter comprises, an elongated sheet of relatively thin flexible material containing a particulate first material dispersed throughout a substantial portion of the sheet, with the sheet extending at least partially around the channel. The sphincter also has a plug having an elongated annular sleeve of elastic material defining a cavity communicating with a port in the plug, such that the sleeve may be inflated in the body channel. The sleeve has a second particulate material dispersed throughout a region in the sleeve, with at least one of the first and second materials comprising a permanent magnetic material, and with the other of the first and second materials comprising a material substantially susceptible to the one magnetic material.

20 Claims, 9 Drawing Figures

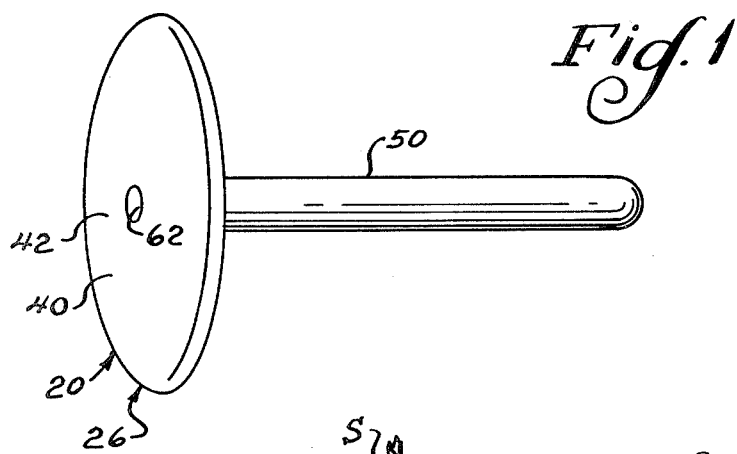
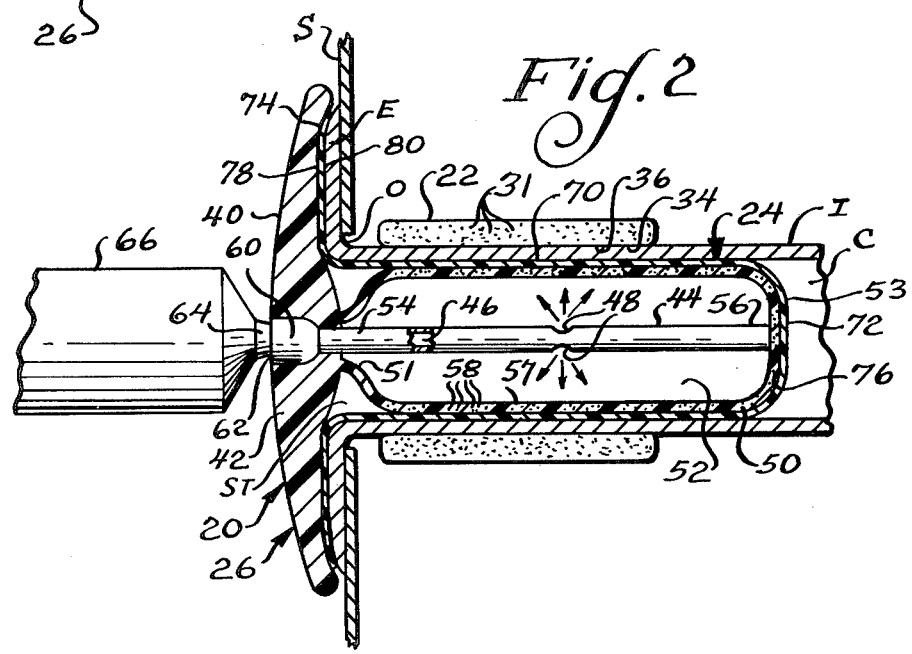
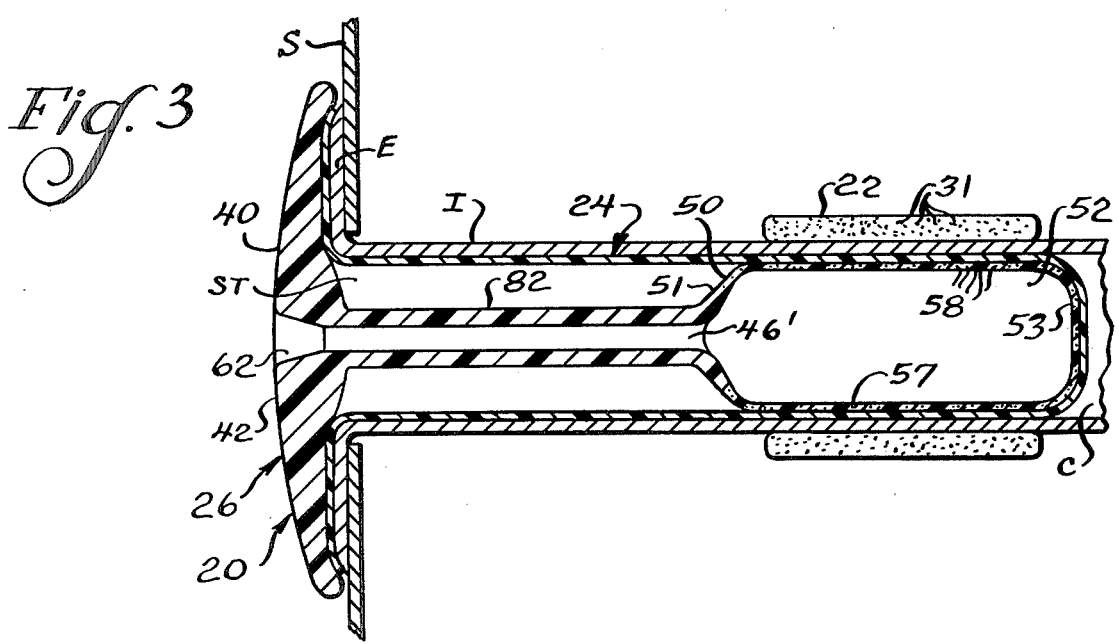

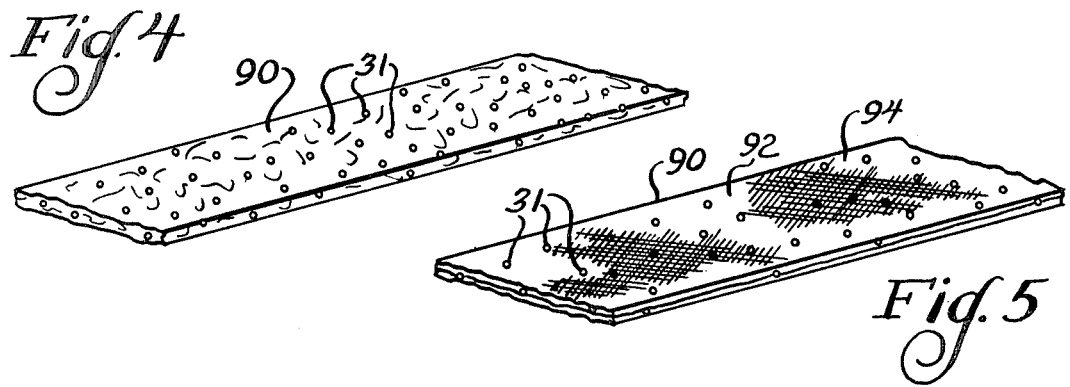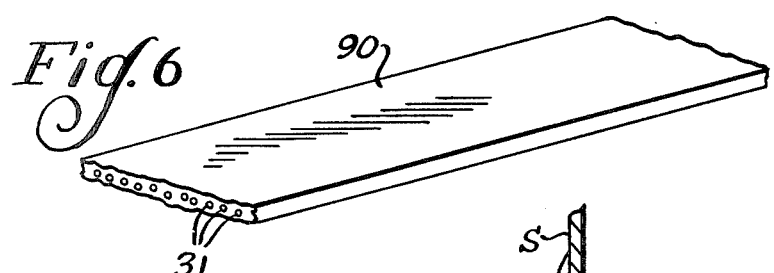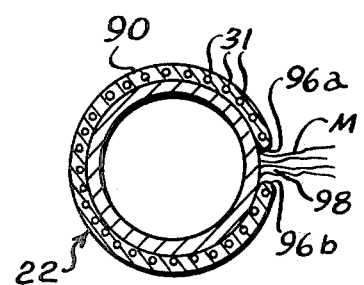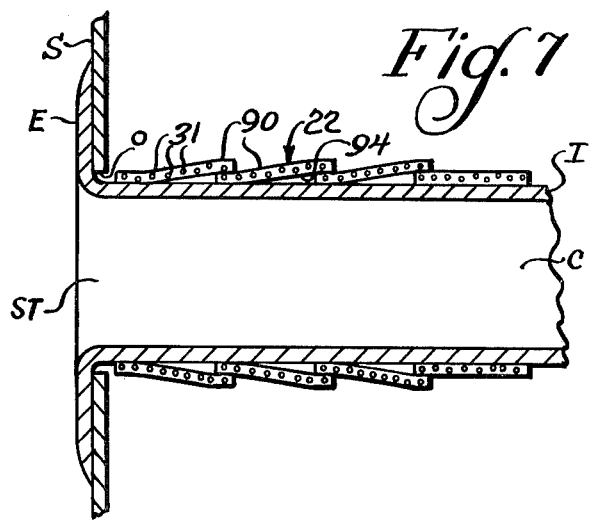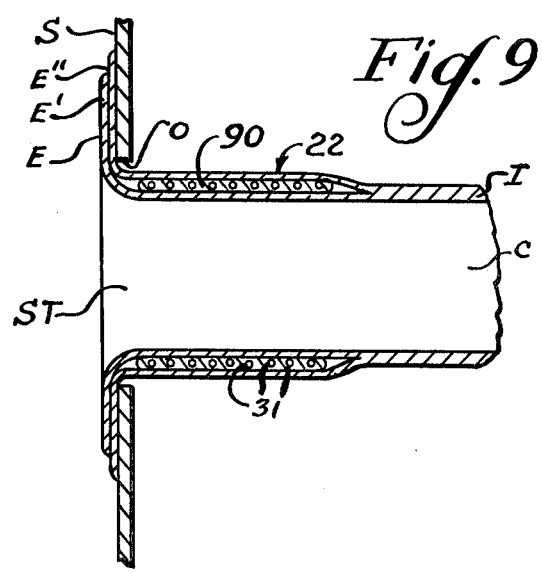

ARTIFICIAL SPHINCTER

BACKGROUND OF THE INVENTION

The present invention relates to closure devices, and more particularly to artificial sphincters.

A large number of temporary and permanent ostomy procedures are undertaken by surgeons each year to correct some difficulty in the intestinal tract, such as an obstruction or cancer in the tract. Most commonly, during the procedure the intestine is severed and an end of the intestine is brought through an incision in the abdominal wall. The surgeon then secures the intestine end adjacent the patient's skin, and forms an opening, termed a "stoma", at the juncture of the intestine and skin to permit passage of faecal matter outside the patient's body. In the case of a colostomy procedure, an end of the colon is joined to the skin to form the stoma. In the case of an ileostomy procedure, an end of the ileum is used to form the stoma, resulting in passage of corrosive fluids containing digestive enzymes and acids outside the patient's body.

The ostomy procedure results in loss of faecal continence for the patient, and typically the patient has been required to wear a pouch on the outside of the body in order to collect the faecal matter passing through the stoma. In an attempt to overcome incontinence, many physicians have advised daily irrigation of the intestine by the patient through the stoma. However, the prior irrigation procedures have been very time consuming and inconvenient, and have not alleviated the need for use of stoma bags in many patients, particularly on social occasions. Surgical attempts have also been made to secure continence, such as by formation of a so-called "Kock Pouch," but the procedures have been accompanied by complications. It has also been proposed to achieve continence with various types of closure devices for the stoma.

SUMMARY OF THE INVENTION

A principal feature of the present invention is the provision of an improved artificial sphincter of simplified construction for closure of an intestine in a patient's body communicating with an opening adjacent the outside of the patient's body.

The sphincter comprises, an elongated sheet of a relatively thin flexible material containing a particulate first material dispersed throughout a substantial portion of the sheet, with the sheet extending at least partially around the intestine. The sphincter has a plug having an outwardly directed rim adjacent a proximal end of the plug, an elongated tubular section extending distally from the rim and defining a lumen, and an elongated annular sleeve of elastic material surrounding a longitudinal portion of the tubular section and defining a cavity communicating with the lumen through aperture means in the tubular section. The sleeve contains a particulate second material dispersed throughout a region of the sleeve, with at least one of the first and second materials comprising a permanent magnetic material, and the other of the first and second materials comprising a material substantially susceptible to the one magnetic material. The plug also has a port communicating with the lumen of the tubular section.

A feature of the present invention is that the sleeve may be inflated through the port in order to position the region of second material in the sleeve adjacent the intestinal walls and the sheet.

Another feature of the invention is that the first and second materials cause flexation of the sleeve against the intestinal walls in a closure position of the plug.

Thus, a feature of the present invention is that the sleeve may be inflated in the patient's body in order to close a channel in the intestine.

Still another feature of the invention is that the sleeve may be deflated in order to remove the plug from the body channel.

A further feature of the invention is that the plug and sheet are relatively light in weight and minimize gravitational forces in the region of the intestine during use of the sphincter.

A feature of the present invention is that the flexible sheet is conformable to the shape of the intestine.

Yet another feature of the invention is that the sheet may comprise a porous material to promote tissue ingrowth of the intestine, such that the sheet becomes integral with the intestine.

A further feature of the invention is that the sheet may be placed by the physician about the intestine in a simplified manner.

Yet another feature of the invention is that the sheet may define a longitudinally extending space to receive the mesentery of the intestine.

Further features will become more fully apparent in the following description of the embodiments of this invention and from the appended claims.

DESCRIPTION OF THE DRAWINGS

In the drawings:

FIG. 1 is a perspective view of a plug for an artificial sphincter of the present invention;

FIG. 2 is an elevational view, taken partly in section, of the plug of FIG. 1 in an inflated configuration;

FIG. 3 is an elevational view, taken partly in section, of another embodiment of a plug for the sphincter of the present invention;

FIG. 4 is a fragmentary perspective view of a sheet of the sphincter for placement around the intestine;

FIG. 5 is a fragmentary perspective view of another embodiment of the sheet for the sphincter of the present invention;

FIG. 6 is a fragmentary perspective view of another embodiment of the sheet for the sphincter of the present invention; and FIGS. 7–9 are sectional views illustrating use of the sheets for placement around the intestine.

DESCRIPTION OF THE PREFERRED EMBODIMENTS

Referring now to FIGS. 1 and 2, there is shown an artificial sphincter generally designated 20 for the intestine, including the colon, having an annular member 22, and a plug 26. With reference to FIG. 2, the annular member 22 has a first material 31 which may be in particulate form, and which may comprise the sheets discussed below in connection with FIGS. 4–9. As shown, during colostomy an outer end E of an intestine I in a patient's body is brought through an opening or incision O adjacent the patient's skin S, with the intestine end E being secured to the patient's skin in order to form a stoma St, and with the annular member 22 extending around the intestine I in the region of the abdominal wall within the patient's skin S, although the member 22 may be constructed to extend only partially around the intestine and for convenience will be termed annular. As shown, the annular member 22 has a relatively smooth inner surface 34 defining an opening 36 in which the intestine is located, with the diameter of the opening 36 being approximately equal to the diameter of the intestine.

With reference to FIGS. 1 and 2, the plug 26 has an outwardly directed circular or annular rim 40 adjacent a proximal end 42 of the plug, such that the rim extends peripherally around the stoma St when the plug 26 is placed in the patient's body. The plug 26 has an elongated tubular section 44 extending distally from the rim 40, with the tubular section 44 defining a lumen 46 and having apertures 48 communicating with the lumen 46. The plug has an elonated annular sleeve 50 of elastic material defining a cavity 52 communicating with the apertures 48 and lumen of the tubular section 44, with a proximal end 51 of the sleeve 50 being connected to the rim 40 or tubular section 44 in a circumferential zone adjacent a proximal end 54 of the tubular section 44, and with a distal end 53 of the sleeve 50 being connected to and closing a distal end 56 of the tubular section 44. The sleeve 50 has a second particulate material 58 dispersed throughout a longitudinal region 57 within the wall of the sleeve 50 itself. In a suitable form, the sleeve 50 may be constructed of a suitable plastic material, and the particulate second material 58 may be placed in the sleeve during extrusion or molding procedures which may be used to construct the sleeve. The plug 26 also has suitable valve means 60 and a port 62 at the proximal end of the plug to receive the tip 64 of a syringe 66, such that the port 62 communicates with the lumen 46 of the tubular section 44 through the valve means 60. The valve means 60 may be of the conventional type which actuates responsive to contact of the syringe tip 64, such that the valve means 60 opens when contacted by the tip 64 of the syringe 66, and closes when the syringe tip 64 is removed from the port 62.

The sphincter 20 may also have a bag or sleeve 24 which may be constructed from any suitable flexible material which is convenient for disposable use, such as a suitable plastic material. The bag 24 has an elongated tubular portion 70, a closed distal end 72, and an annular outwardly flared proximal portion 74, with the bag 24 defining a cavity 76 to receive a distal portion of the plug 26. Prior to placement of the plug 26 in the intestine, a bag 24 may be placed over the plug in order to protect the plug from corrosive fluids and minimize soiling of the plug during use. After removal of the plug from the patient's body, the soiled bag 24 may be removed from the plug and may be discarded, after which a new bag may be placed on the plug for subsequent use of the device. If desired, the bag 24 may have attachment means 78, such as areas of adhesive, for releasably attaching the bag proximal portion 74 to the plug rim 40. Also, if desired, the proximal portion 74 of the bag 24 may have attachment means 80, such as regions of adhesive, for securement of the bag 24 to the intestine I or skin S in a releasable manner.

At least one of said first and second materials 31 and 58 comprises a permanent magnetic material, such as a samariumcobalt magnetic material, while the other of the first and second materials 31 and 58 comprises a material which is substantially susceptible to the one magnetic material, such as a magnetic material or a ferromagnetic material. With respect to magnetic properties, substances are generally classified as ferromagnetic, paramagnetic, and diamagnetic materials. A permeability $\mu$ is associated with substances, where $\mu = \mu_o$ for a vacuum ($\mu_o/4\pi = 10-7$ Weber/amp-m.), $\mu$ is slightly greater than $\mu_o$ for paramagnetic materials, $\mu$ is slightly smaller than $\mu_o$ for diamagnetic materials, and $\mu$ is often much larger than $\mu_o$ for ferromagnetic materials. Apparently, iron, nickel and cobalt are technically considered the only ferromagnetic materials, but certain alloys display similar properties. Hence, for purposes under discussion, the term "ferromagnetic" will be taken in a broader sense to include materials which display properties akin to the classified ferromagnetic materials.

In use, a bag 24 is placed in position over the plug 26, and the distal parts of the bag and plug are inserted into a channel C of the intestine I. Next, with reference to FIG. 2, the syringe tip 64 is inserted through the port 62 in order to contact and open the valve means 60. A suitable fluid, such as air, may then be pumped by the syringe 66 through the open valve means 60 and the tubular section 44 into the cavity 52 in order to inflate the sleeve 50. After sufficient inflation of the sleeve or balloon 50, the susceptibility of the particulate second material 58 in the sleeve wall relative to the first material 31 in the annular member 22, in combination with the elasticity of the plug sleeve wall, causes the plug to assume a closure position with the sleeve slightly engaging against the wall of the intestine I through the bag 24 in the region around the annular member 22. In this configuration, the plug 26 seals the stoma St and closes the channel C in the intestine I. The syringe tip 64 may be removed from the valve means 60 in order to permit closure of the valve means and maintain the sleeve 50 inflated during use of the sphincter by the patient. When it is desired to remove the plug from the patient's body, the syringe tip 64 may be inserted through the port 62 into the valve means 60 in order to open the valve means 60 and withdraw the fluid from the sleeve cavity 52, thus permitting removal of the sleeve wall from the intestine and removal of the plug from the body.

Thus, in accordance with the present invention, the plug may be utilized to close the stoma St of the intestine I during prolonged periods of time. The inflated sleeve 50 conforms to the shape of the intestine and minimizes the possibility of necrosis or other harm to the intestine during use of the plug. In this regard, it is noted that the sleeve need only be inflated a sufficient amount to place the sleeve wall in close proximity to the annular member 22, after which the first and second materials 31 and 58 cause the sleeve wall to assume a sealing configuration in the intestine. Moreover, the plug of the present invention is relatively light in weight in order to minimize gravitational forces in the region of the stoma St which otherwise might cause harm to the intestine and discomfort to the patient. Further, the plug of the invention may be readily placed in and removed from the intestine channel C through use of the syringe in a manner as previously described.

Another embodiment of the plug 26 of the present invention is illustrated in FIG. 3, in which like reference numerals designate like parts. In this embodiment, the annular member 22 is positioned at a location substantially spaced from the patient's skin S in the peritoneum. Accordingly, the plus has an elongated central portion 82 extending intermediate the rim 40 at the proximal end 42 of the plug 26 and the proximal end 51 of the sleeve 50, such that the sleeve 50 is spaced a substantial distance from the plug rim 40 and is positioned within the annular member 22 in a closure position of the plug.

In this embodiment, the plug has a port 62 communicating with a lumen 46' of the central portion 82, but the valve means previously discussed in connection with the embodiment of FIGS. 1 and 2 has been omitted. Also, as shown, the tubular section 44 may be omitted from this embodiment, as well as the embodiment of FIGS. 1 and 2, if desired. Thus, in this embodiment the sleeve 50 is inflated directly through the port 62 a sufficient amount in order to position the sleeve wall in the proximity of the annular member 22, after which the susceptibility of the first and second materials 31 and 58 cause the sleeve 50 of the plug 26 to assume a sealing configuration. The syringe may then be removed from the plug, and the plug sleeve 50 maintains a sealing configuration even though the lumen 46 in the central portion 82, which communicates with the sleeve cavity 52, is open to the atmosphere. After use of the plug, the syringe may be utilized to deflate the sleeve 50 in order to facilitate removal of the plug from the intestine channel.

With reference to FIG. 7, in accordance with another aspect of the present invention, the annular member 22 may comprise an elongated sheet or strip 90 of a relatively thin flexible material containing a particulate first material 31. As shown, the sheet 90 may be helically wrapped around the outer surface of the intestine I during formation of the stoma St. Thus, the sheet 90 may be placed as desired by the physician for a particular patient in a simplified manner.

With reference to FIG. 4, the sheet 90 may comprise an elongated strip of nonwoven material containing the first particulate material 31. In an alternative form, as shown in FIG. 5, the sheet 90 may comprise a porous material, such as a woven fabric, or may have an inner layer 92 of a porous fabric defining an inner surface 94 for facing the outer surface of the intestine in order to promote tissue ingrowth of the intestine into the sheet 90. In this manner, the sheet 90 defining the annular member 22 may become an integral part of the intestine during healing of the patient. In a further form, as shown in FIG. 6, the sheet 90 may comprise an elongated strip of a suitable flexible plastic material containing the first particulate material 31, and may be constructed in a simplified manner by extrusion. Also, if desired, the sheet 90 may be elastic.

With reference to FIG. 7, after the sheet 90 has been wrapped about the intestine I, the flexible sheet permits movement of the intestinal wall during use of the plug in its closure position, thus minimizing the possibility of trauma to the intestine and possible necrosis. Further, the sheet 90 is relatively light in weight, and minimizes the gravitational forces in the region of the intestine.

With reference to FIG. 8, in an alternative form, the sheet 90 may comprise a longitudinal section which extends circumferentially around a longitudinal segment of the intestine, with the sheet having a pair of opposed side edges 96a and 96b defining a longitudinally extending space 98 to receive the mesentery M of the intestine I. In the previous arrangement discussed in connection with FIG. 7, the mesentery is removed from the intestine by the physician in the region where the sheet 90 is wrapped. In a further form, as shown in FIG. 9, the physician may longitudinally split the intestine end E in order to form bifurcated intestine ends E' and E'', after which a segment of the sheet 90 may be placed intermediate the bifurcated intestine ends E' and E'', and the ends E' and E'' may be secured to the patient's body while enclosing the annular sheet segment.

Of course, the plug previously described in connection with FIGS. 1-3 may be utilized with the sheet 90 discussed in connection with FIGS. 4-9 or a susceptible plug of similar nature. The size of the particulate material 31 of the sheet 90 may vary from relatively small granules in the sheet itself to larger separate segments of the first material which do not unduly impair the flexibility of the sheet, and which may be secured on a surface of the sheet, if desired.

The foregoing detailed description is given for clearness of understanding only, and no unnecessary limitations should be understood therefrom, as modifications will be obvious to those skilled in the art.

We claim:

1. An artificial sphincter for closure of an intestine in a patient's body communicating with an opening adjacent the outside of the patient's body, comprising:
   an elongated sheet of a relatively thin flexible material containing a particulate first material dispersed throughout a substantial portion of the sheet, said sheet extending at least partially around a channel in the intestine; and
   a plug having an insertion portion for placement in the intestine channel and containing a second material, with at least one of said first and second materials comprising, a permanent magnetic material, and the other of said first and second materials comprising a material substantially susceptible to said one magnetic material.

2. The sphincter of claim 1 wherein said first material comprises a permanent magnetic material.

3. The sphincter of claim 1 wherein said sheet comprises a nonwoven material.

4. The sphincter of claim 1 wherein said sheet comprises a plastic material.

5. The sphincter of claim 1 wherein said sheet comprises a porous material.

6. The sphincter of claim 5 wherein said sheet comprises a fabric.

7. The sphincter of claim 1 wherein an inner surface of said sheet comprises a layer of porous material, said inner surface adapted to face an outer surface of the intestine.

8. The sphincter of claim 1 wherein said sheet comprises an elongated helically wrapped strip, an inner surface of said sheet adapted to face an outer surface of a longitudinal section of the intestine.

9. The sphincter of claim 1 wherein said sheet includes a pair of opposed sides defining a longitudinal space, said sheet adapted to extend circumferentially around an outer surface of a longitudinal section of the intestine, said pair of opposed sides adapted to receive the mesentery of the intestine.

10. The sphincter of claim 1 wherein said sheet is adapted for placement intermediate bifurcate end portions of the intestines.

11. An artificial sphincter for closure of a channel in a patient's body communicating with an opening adjacent the outside of the patient's body, comprising:
   a generally annular member containing a first material for placement at least partially around the channel of the patient's body; and
   a plug having an elongated flexible sidewall of an elastic material for placement within said annular member with said sidewall facing toward walls of said channel, said sidewall containing a particulate second material dispersed through a region in said sidewall, with at least one of said first and second materials comprising a permanent magnetic material, and with the other of said first and second materials comprising a material substantially susceptible to said one magnetic material, said sidewall defining a cavity, and said plug having port means communicating with said cavity to permit inflation of said sidewall.

12. The sphincter of claim 11 wherein said plug has an elongated tubular section communicating with said port means, with said tubular section having a lumen communicating with said cavity through aperture means in the tubular section.

13. The sphincter of claim 12 wherein said sidewall comprises an annular sleeve surrounding said tubular section.

14. The sphincter of claim 13 wherein a proximal portion of said sleeve is spaced a substantial distance distally from a proximal portion of the plug.

15. The sphincter of claim 11 wherein said plug includes an outwardly directed rim adjacent a proximal end of the plug for placement peripherally around said opening outside the patient's body.

16. The sphincter of claim 11 wherein said plug includes valve means intermediate said port means and said cavity.

17. The sphincter of claim 16 wherein said valve means is actuatable responsive to contact of the valve means.

18. The sphincter of claim 11 wherein said annular member comprises an elongated sheet of flexible material containing said first material dispersed throughout a substantial portion of said sheet.

19. An artificial sphincter for closure of a channel in a patient's body communicating with an opening outside the patient's body, comprising:

a generally annular member containing a first material for placement at least partially around the channel of the patient's body; and a plug having an outwardly directed rim adjacent a proximal end of the plug, an elongated tubular section extending distally from said rim and defining a lumen, an elongated annular sleeve of elastic material surrounding a longitudinal portion of said tubular section and defining a cavity communicating with said lumen through aperture means in the tubular section, said sleeve containing a particulate second material dispersed through a region of said sleeve, with at least one of said first and second materials comprising a permanent magnetic material, and the other of said first and second materials comprising a material substantially susceptible to said one magnetic material, and said plug having port means communicating with said lumen to permit inflation of said annular member.

20. The sphincter of claim 19 wherein said plug includes valve means intermediate said port means and lumen.